US011160897B1

(12) United States Patent
Shalvi

(10) Patent No.: US 11,160,897 B1
(45) Date of Patent: Nov. 2, 2021

(54) ULTRAVIOLET DISINFECTION DEVICE AND USES THEREOF

(71) Applicant: OLYMPIA LIGHTING, INC., Northvale, NJ (US)

(72) Inventor: Ram Shalvi, Closter, NJ (US)

(73) Assignee: OLYMPIA LIGHTING, INC., Northvale, NJ (US)

( * ) Notice: Subject to any disclaimer, the term of this patent is extended or adjusted under 35 U.S.C. 154(b) by 0 days.

(21) Appl. No.: 17/327,122

(22) Filed: May 21, 2021

Related U.S. Application Data

(60) Provisional application No. 63/029,378, filed on May 22, 2020.

(51) Int. Cl.
| | |
|---|---|
| A61L 9/20 | (2006.01) |
| F21V 29/61 | (2015.01) |
| F21K 9/232 | (2016.01) |
| F21V 21/26 | (2006.01) |
| H05B 45/18 | (2020.01) |
| H05B 45/50 | (2020.01) |
| A61L 2/26 | (2006.01) |
| A61L 2/24 | (2006.01) |
| A61L 2/10 | (2006.01) |
| F21V 23/04 | (2006.01) |
| F21Y 113/10 | (2016.01) |
| F21Y 115/10 | (2016.01) |
| F21Y 103/10 | (2016.01) |
| F21Y 107/30 | (2016.01) |

(52) U.S. Cl.
CPC .............. *A61L 9/20* (2013.01); *A61L 2/10* (2013.01); *A61L 2/24* (2013.01); *A61L 2/26* (2013.01); *F21K 9/232* (2016.08); *F21V 21/26* (2013.01); *F21V 23/0471* (2013.01); *F21V 29/61* (2015.01); *H05B 45/18* (2020.01); *H05B 45/50* (2020.01); *A61L 2202/11* (2013.01); *A61L 2202/14* (2013.01); *A61L 2209/111* (2013.01); *A61L 2209/12* (2013.01); *A61L 2209/15* (2013.01); *F21Y 2103/10* (2016.08); *F21Y 2107/30* (2016.08); *F21Y 2113/10* (2016.08); *F21Y 2115/10* (2016.08)

(58) Field of Classification Search
USPC .................................................. 250/454.11
See application file for complete search history.

(56) References Cited

U.S. PATENT DOCUMENTS

| | | |
|---|---|---|
| 3,744,216 A | 7/1973 | Halloran |
| 3,750,370 A | 8/1973 | Brauss et al. |
| 5,505,904 A | 4/1996 | Haidinger et al. |
| 6,464,760 B1 | 10/2002 | Sham et al. |
| 6,494,940 B1 | 12/2002 | Hak |
| 7,270,696 B2 | 9/2007 | Yuen |
| 7,296,913 B2 * | 11/2007 | Catalano ............ H05B 45/3725 |
| | | 362/257 |
| 8,252,100 B2 | 8/2012 | Worrilow |
| 8,350,228 B2 | 1/2013 | Welker |
| 8,377,183 B2 | 2/2013 | Bailey et al. |
| 8,562,913 B2 | 10/2013 | Searle |
| D721,828 S * | 1/2015 | Chen ................................ D26/2 |
| 8,926,132 B2 | 1/2015 | Horng et al. |
| D735,903 S * | 8/2015 | Li ..................................... D26/2 |
| 9,115,883 B1 * | 8/2015 | Martin ..................... F21K 9/23 |
| 9,140,441 B2 * | 9/2015 | Goelz ..................... F21V 13/02 |
| 9,308,289 B2 | 4/2016 | Graff et al. |
| D762,884 S | 8/2016 | Shalvi |
| 9,517,280 B2 | 12/2016 | Lynn et al. |
| 9,517,284 B1 * | 12/2016 | Stibich ..................... A61L 2/14 |
| D782,081 S * | 3/2017 | Shalvi ............................. D26/2 |
| 9,603,956 B2 | 3/2017 | Newham |
| 9,707,310 B2 | 7/2017 | Watanabe et al. |
| D819,839 S * | 6/2018 | Shalvi ............................. D26/2 |
| D819,840 S * | 6/2018 | Shalvi ............................. D26/2 |
| 10,039,852 B2 | 8/2018 | Yi et al. |
| 2008/0008620 A1 | 1/2008 | Alexiadis |
| 2013/0215620 A1 * | 8/2013 | Zhou ..................... F21V 21/14 |
| | | 362/285 |
| 2017/0321877 A1 | 11/2017 | Polidoro |
| 2018/0064840 A1 | 3/2018 | Saiki et al. |
| 2018/0250430 A1 | 9/2018 | Machovina et al. |
| 2018/0299117 A1 | 10/2018 | Min |
| 2019/0234563 A1 | 8/2019 | Cartiere et al. |
| 2020/0009286 A1 | 1/2020 | Zarcone et al. |
| 2020/0030478 A1 | 1/2020 | Uchimura |
| 2020/0282086 A1 * | 9/2020 | Silverman ............ A61N 5/0624 |
| 2020/0289698 A1 * | 9/2020 | Polidoro ................. F21V 21/04 |

FOREIGN PATENT DOCUMENTS

| | | |
|---|---|---|
| CN | 103353146 A | 10/2013 |
| CN | 209262813 U | 8/2019 |
| CN | 209944154 U | 1/2020 |
| CN | 111330033 A | 6/2020 |
| CN | 111365651 A | 7/2020 |
| CN | 111536468 A | 8/2020 |
| CN | 111542149 A | 8/2020 |
| CN | 211450402 U | 9/2020 |
| EP | 2881126 A1 | 6/2015 |
| KR | 20030048989 A | 6/2003 |
| KR | 100698800 B1 | 3/2007 |
| KR | 20090078908 A | 7/2009 |
| KR | 20100119627 A | 11/2010 |

(Continued)

*Primary Examiner* — Phillip A Johnston
(74) *Attorney, Agent, or Firm* — Law Offices of Albert Wai-Kit Chan, PLLC; Robert D. Katz, Esq.

(57) ABSTRACT

The present invention provides a device for generating ultraviolet (UV) radiation whose wavelength is optimally tuned into the range of 240 to 290 nm, with peak wavelength in the range of 260 to 270 nm, which attains a Peak Germicidal Disinfection Effective Index of nearly 100%, superior to conventional UV lights and lamps. This device comprises a light-emitting diode (LED) matrix, a fan, an LED driver, a base and a motion sensor with programmable sensitivity and time delay. It may further comprise components for thermal protection and active air circulation. When operating, the device emits visible UVA radiation and blue light. With special considerations for user safety, the device effectively protects users from exposure to UV hazards and is safe to use. With the built-in thermal protection, this device may be used with either open or enclosed fixtures.

20 Claims, 15 Drawing Sheets

(56) References Cited

FOREIGN PATENT DOCUMENTS

| | | |
|---|---|---|
| KR | 101338130 B1 | 12/2013 |
| TW | M513332 U | 12/2015 |
| WO | 2020052506 A1 | 3/2020 |

* cited by examiner

FIGURE 3B
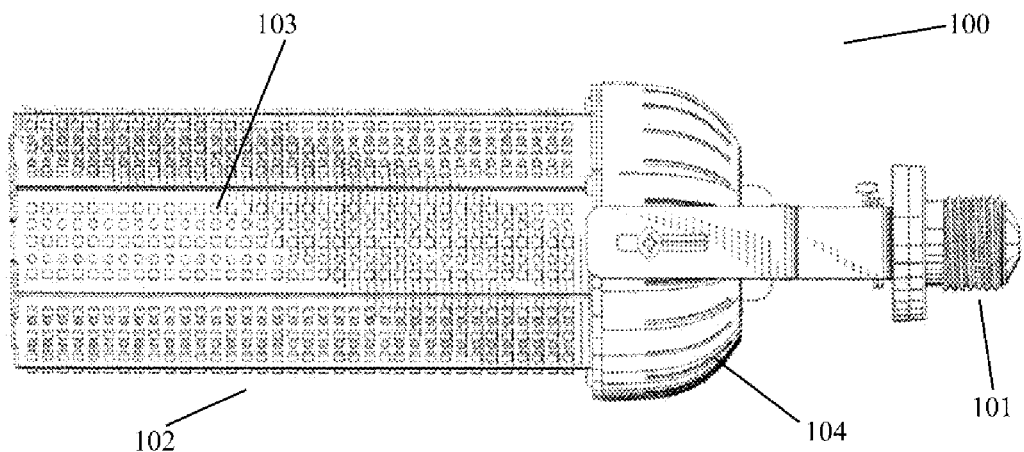
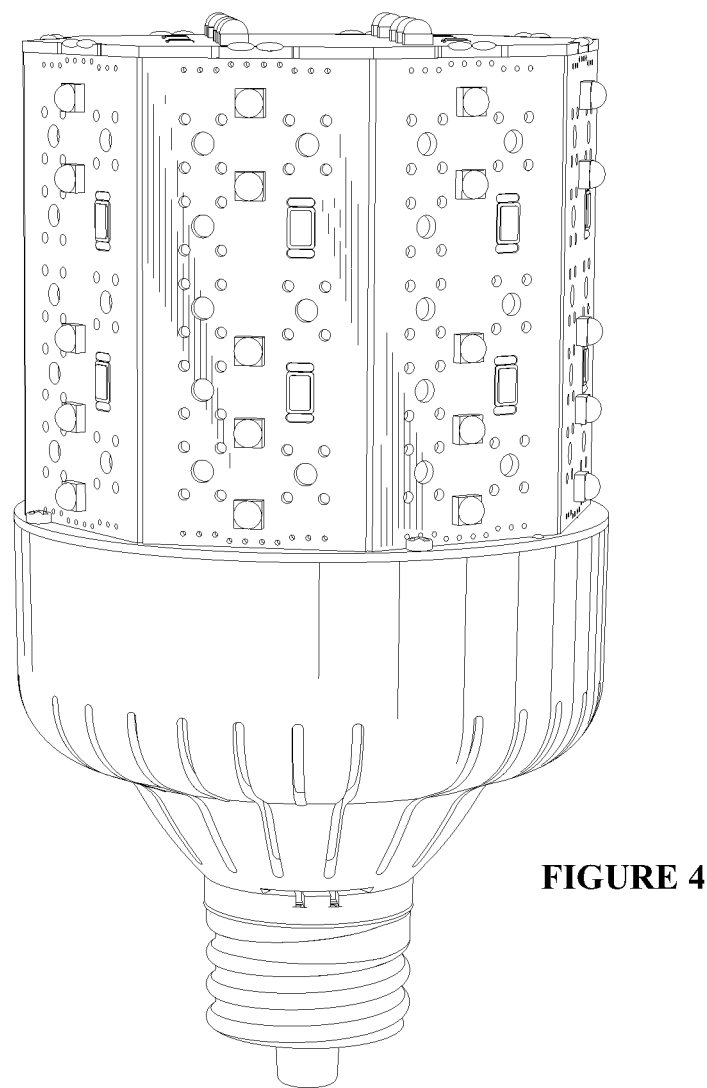
FIGURE 4

FIGURE 12

ULTRAVIOLET DISINFECTION DEVICE AND USES THEREOF

CROSS-REFERENCE TO RELATED APPLICATION

This application claims the benefits of U.S. Ser. No. 63/029,378, filed May 22, 2020. The entire contents and disclosures of the prior application are incorporated herein by reference into this application.

Throughout this application, various references are referred to and disclosures of these publications in their entireties are hereby incorporated by reference into this application to more fully describe the state of the art to which this invention pertains.

FIELD OF THE INVENTION

The present invention relates to lighting devices that include germicidal disinfection by ultraviolet radiation.

BACKGROUND OF THE INVENTION

Ultraviolet (UV) radiation can be utilized for germicidal disinfection. UV radiation is the electromagnetic radiation that falls in the region of spectrum between visible light and x-rays. UV radiation is invisible to the human eye and includes wavelength in the spectral range of 100 to 400 nanometers (nm). This spectral range can be subdivided into four regions: vacuum UV rays with wavelength in the range of 100 to 200 nm, UVC rays with wavelength range of 200 to 280 nm, UVB rays with wavelength range 280 to 315 nm, and UVA rays with wavelength range 315 nm to 400 nm. Because of the spectral sensitivity of DNA and RNA in bacteria and viruses, only the UVC region demonstrates significant germicidal properties.

Conventional devices using UV radiation for disinfection, such as low-pressure UV lights and/or UV lamps, may have present problems with safety and effectiveness. Extensive and prolonged exposure to UV radiation may be associated with occurrence of skin cancers and may also cause problems to health of eyes. The effectiveness index of a conventional UV lamp is typically around 80%, not having put the UVC region into most effective use. The present invention solves foregoing issues with innovative designs and optimal spectral tuning.

SUMMARY OF THE INVENTION

The present invention provides a disinfection device comprising: a base; a plurality of ultraviolet light sources arranged in a predetermined pattern to form an ultraviolet unit; a bowl-shape housing having two ends, wherein one end is smaller than the other end, wherein the smaller end of the housing is mounted on the base, and the light array the ultraviolet unit are mounted on the other end of the housing. The device also includes a means for thermal protection; a means for motion detection; and a circuit to convert commercial power provided through the base into power for the light array and the ultraviolet unit, the means for thermal protection, and the means for motion detection. The means for thermal protection, the means for motion detection, and the circuit are included within the housing. The means for thermal protection maintains the device at an operating temperature that prevents overheating. The means for motion detection detects motion of a human in proximity to the device and switches off the ultraviolet light source so as not to expose the subject to ultraviolet light when the subject is in the vicinity of the ultraviolet light source. When the person leaves the vicinity of the ultraviolet light source, the motion sensor reactivates the ultraviolet light source once again to generate ultraviolet radiation that projects outwards and disinfects surrounding surfaces and air.

In one embodiment, the UV radiation generated by the light sources (e.g., LEDs including ultraviolet LEDs) is in the wavelength range of 200 nm to 400 nm. In one embodiment, the UV radiation generated by the light sources (e.g., LEDs including ultraviolet LEDs) is in the wavelength range of 240 nm to 290 nm. In another embodiment, the UV radiation generated by the light sources (e.g., LEDs including ultraviolet LEDs) has peak wavelength range of 260 nm to 270 nm. In one embodiment, the UV radiation kills germs including bacteria and viruses and disinfects surrounding air and surfaces.

BRIEF DESCRIPTION OF THE FIGURES

FIG. 3B is a side view of the disinfection device shown in FIG. 3A.

FIG. 4 is a front view of the disinfection device in one embodiment of the present invention.

Figure 12:
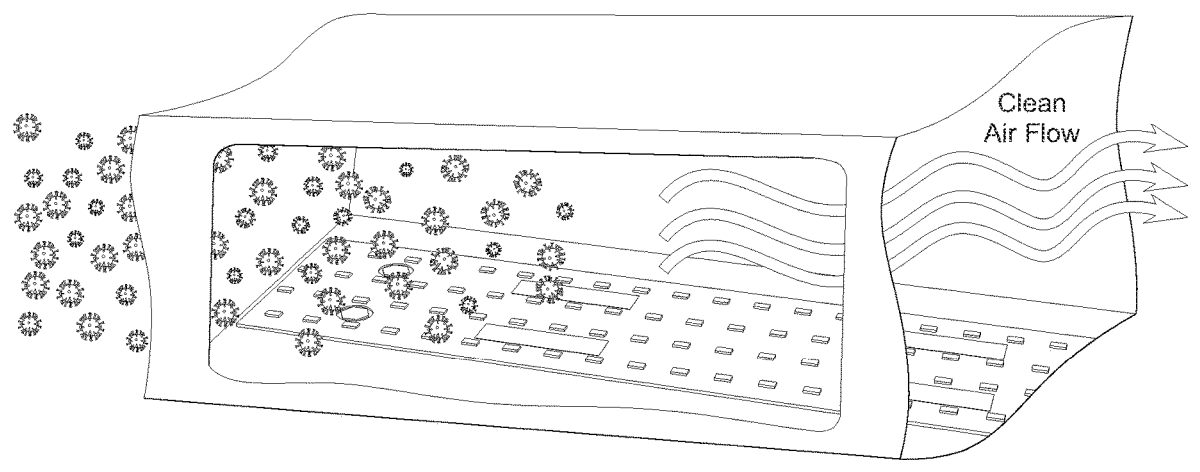

FIG. 12 illustrates an air duct with the device of the present invention equipped therewith for disinfection. Mounted onto the bottom panel of the duct are the light sources that are capable of emitting disinfecting ultraviolet radiation.

FIGS. 13D and 13E show the LEDs arranged in a typical LED strip.

FIG. 13F is a typical UV LED PCB electrical diagram in an air purifier.

DETAILED DESCRIPTION OF THE INVENTION

Figure 1A:
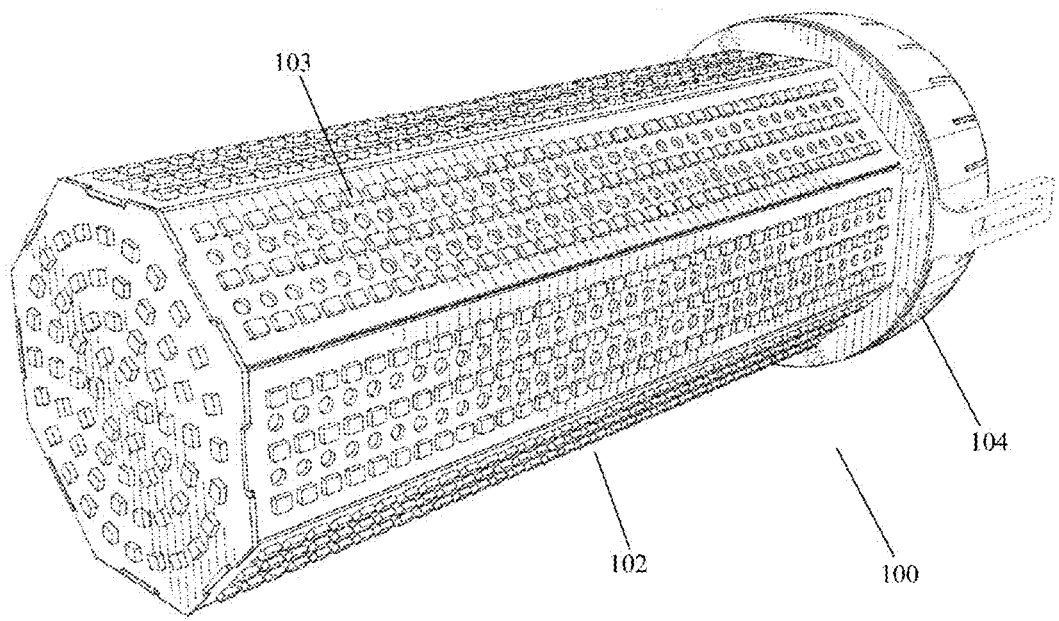
FIG. 1A is a perspective view of one embodiment of the disinfection device of the present invention.
Figure 1B:
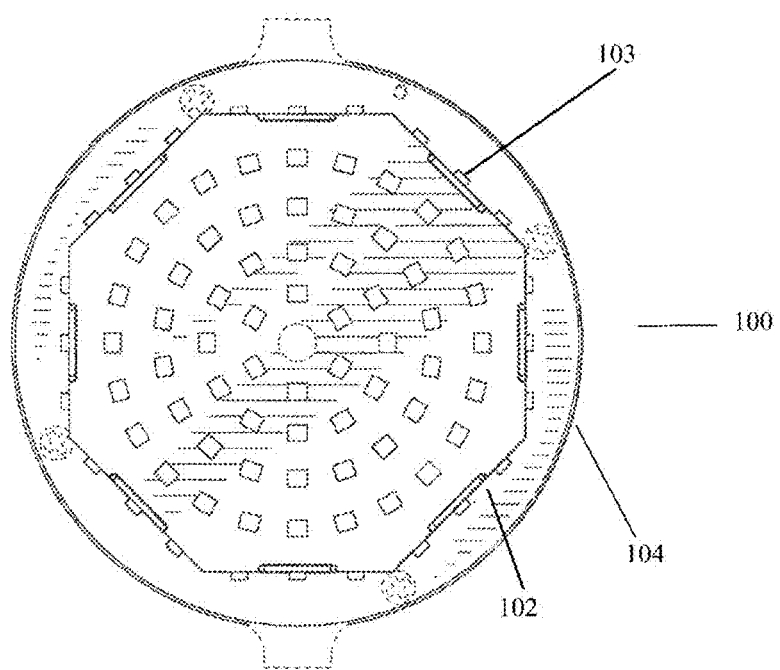
FIG. 1B is a front view of the disinfection device shown in FIG. 1A.
Figure 1C:
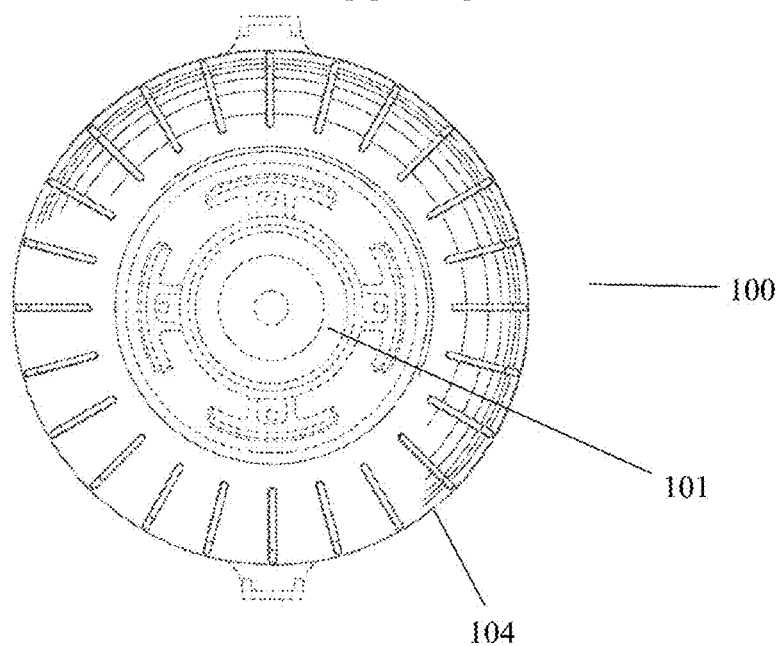
FIG. 1C is an end view of the disinfection device shown in FIG. 1A.
Figure 2A:
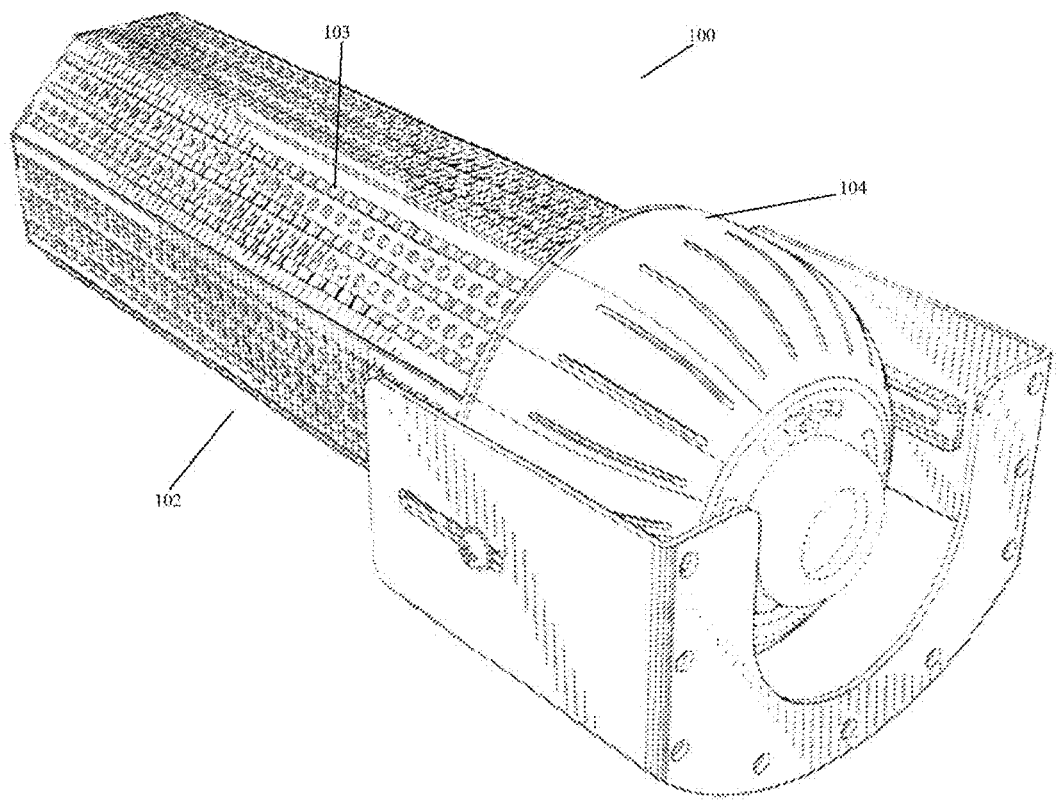
FIG. 2A is a perspective view of the disinfection device in one embodiment of the present invention.
Figure 2B:
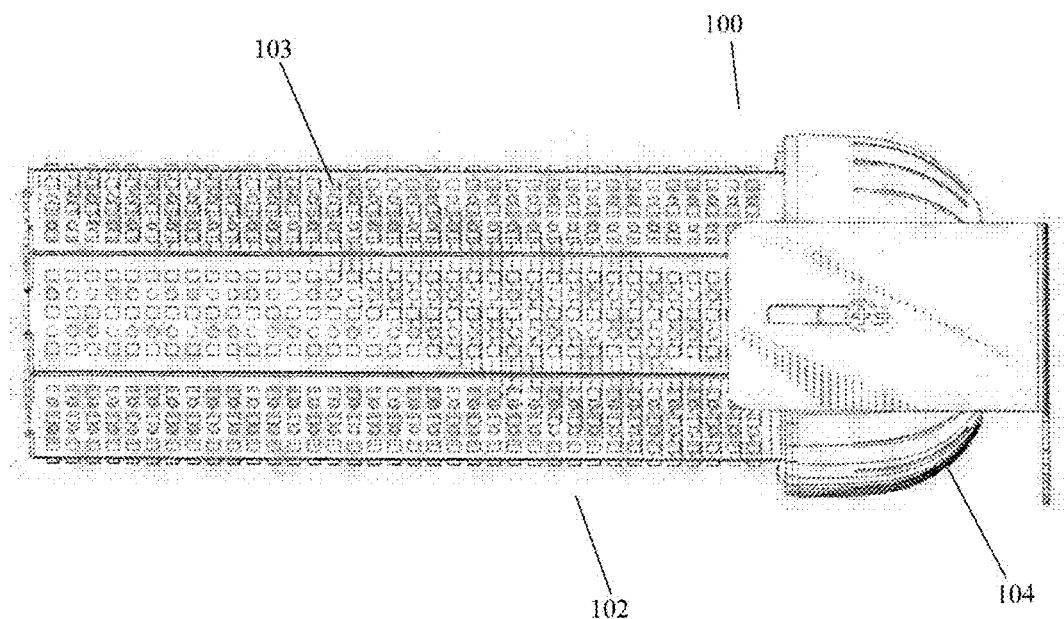
FIG. 2B is a side view of the disinfection device shown in FIG. 2A.
Figure 2C:
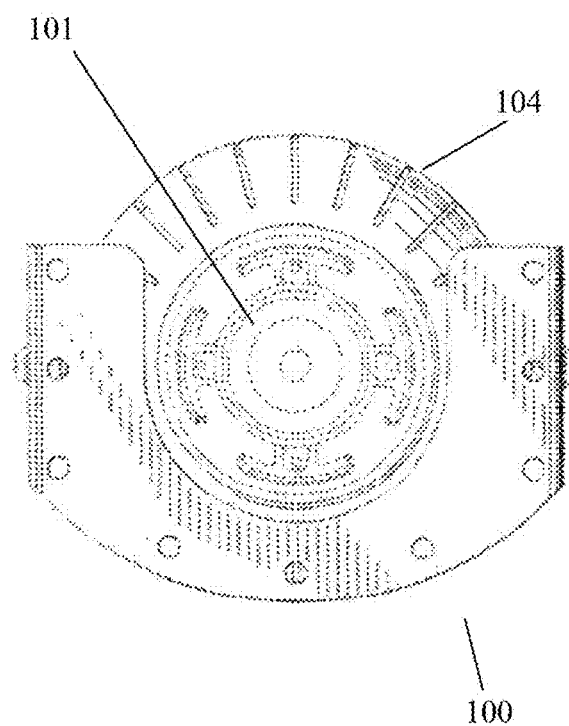
FIG. 2C is an end view of the disinfection device shown in FIG. 2A.
Figure 2D:
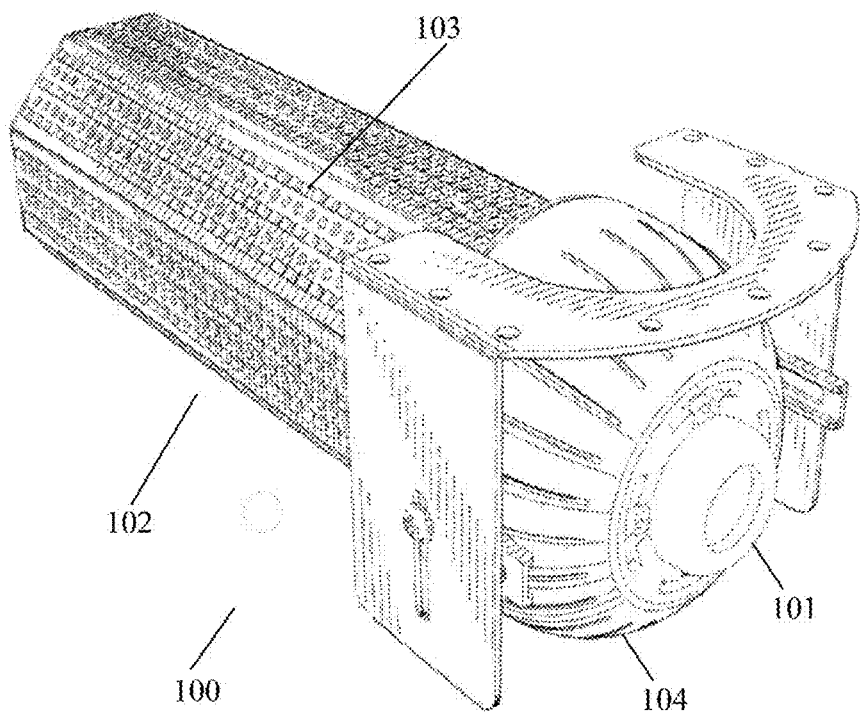
FIG. 2D is a perspective view of the disinfection device shown in FIG. 2A, viewed from a different perspective angle.
Figure 3A:
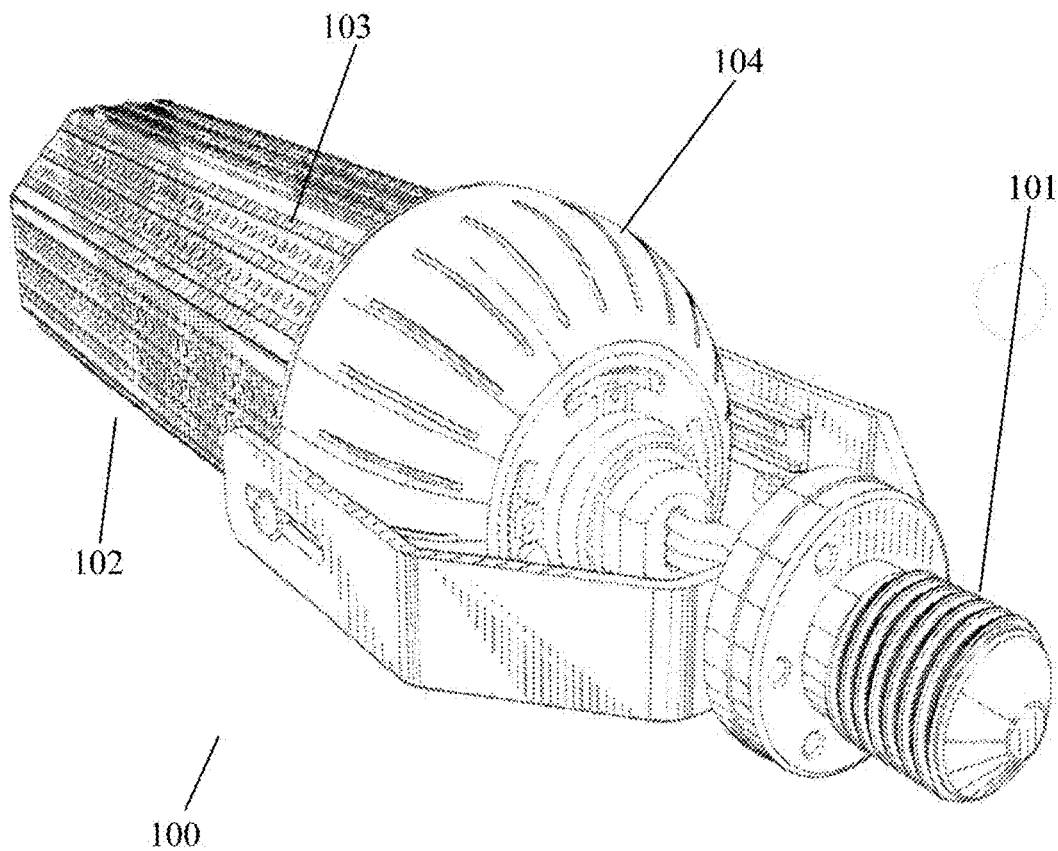
FIG. 3A is a perspective view of the disinfection device in one embodiment of the present invention.
Figure 5A:
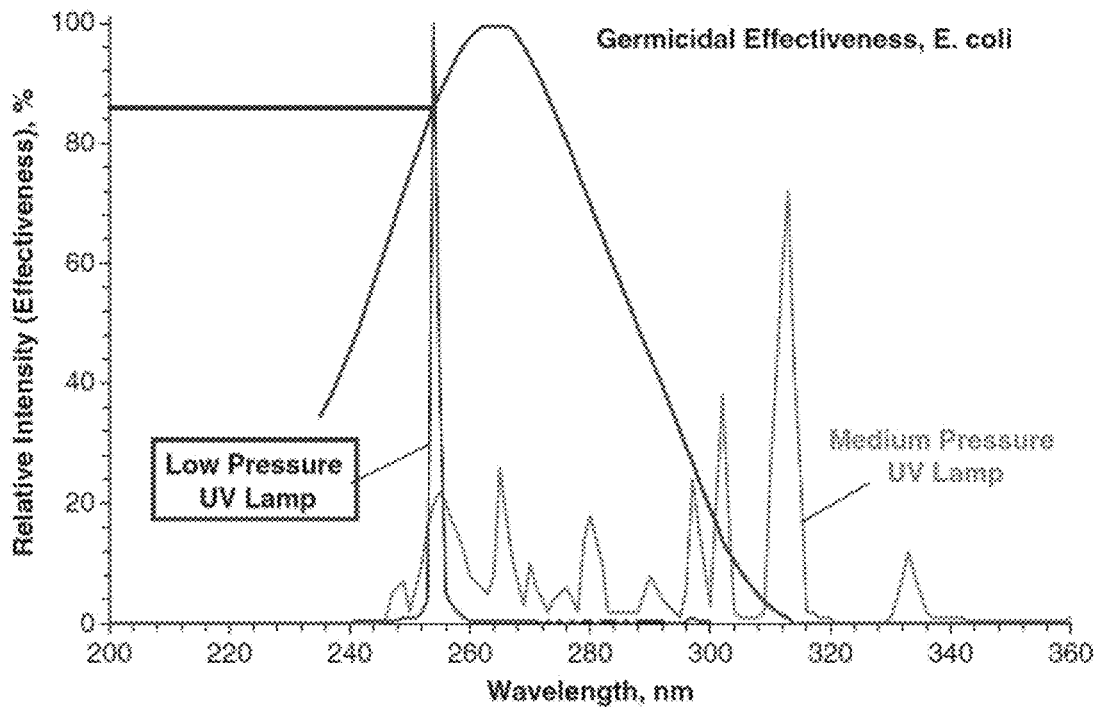
FIG. 5A is a spectrum diagram of conventional low-pressure UV lights/lamps, showing Peak Germicidal Disinfection Effectiveness as measured by peak relative intensity approximately 80%.
Figure 5B:
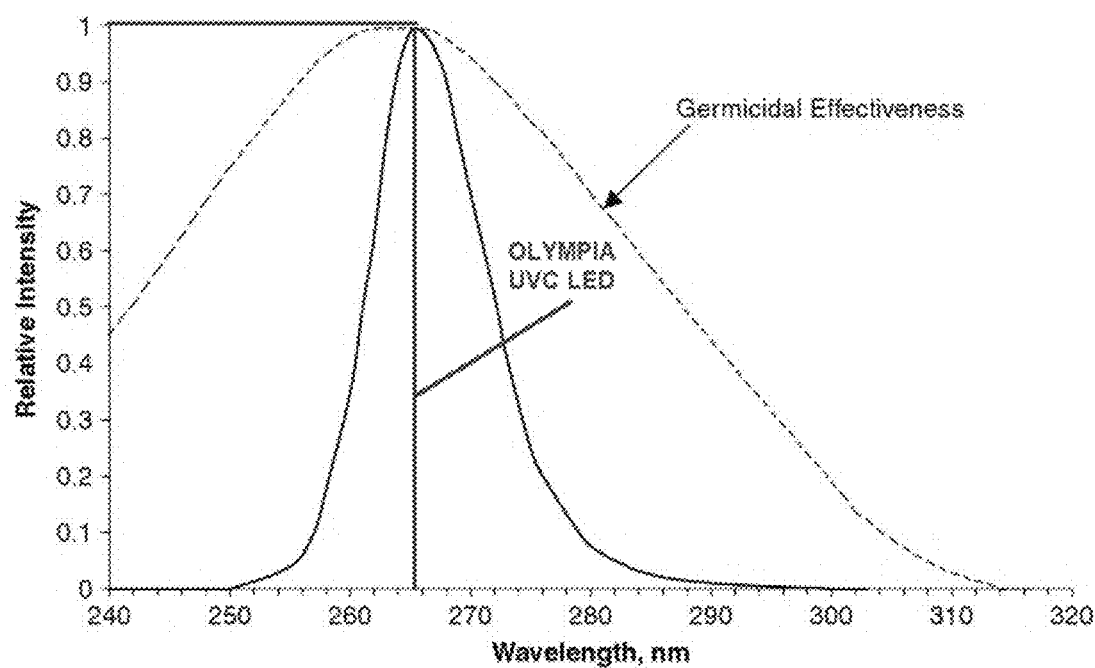
FIG. 5B is a spectrum diagram of the disinfection device of present invention, showing a wavelength range of 250 nm to 300 nm and Peak Germicidal Disinfection Effectiveness close to 100%.
Figures 6A, 6B, 6C:
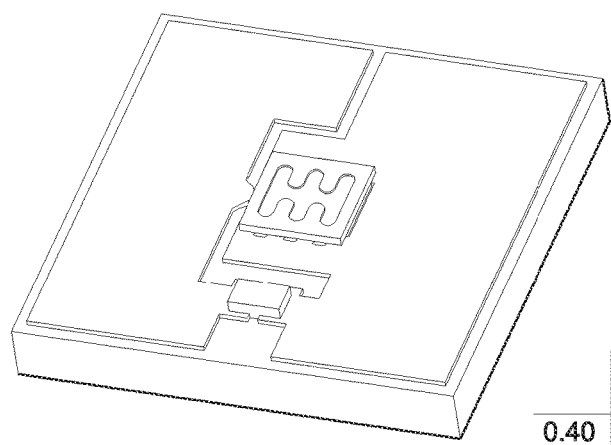
FIG. 6A is a perspective view of an LED in one embodiment of the present invention including a back panel comprising the cathode, the anode, and the thermal plates.
FIG. 6B is a top view of the LED back panel shown in FIG. 6A.
FIG. 6C is a top view of the LED back panel shown in FIG. 6A.
Figure 6D:
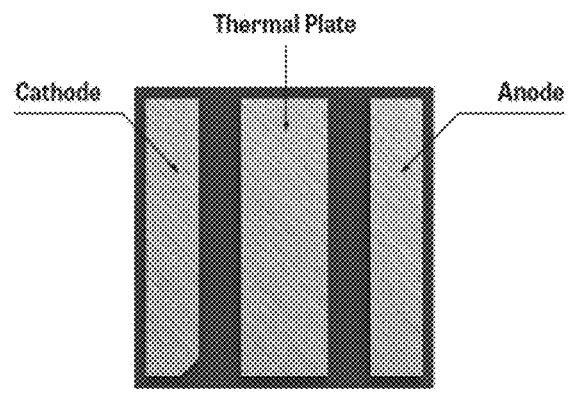
FIG. 6D is a top view of the LED back panel shown in FIG. 6A.
Figure 6E:
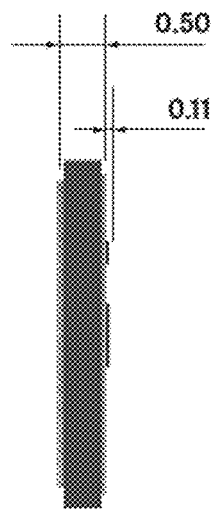
FIG. 6E is a side view of the LED shown in FIG. 6A.
Figure 6F:
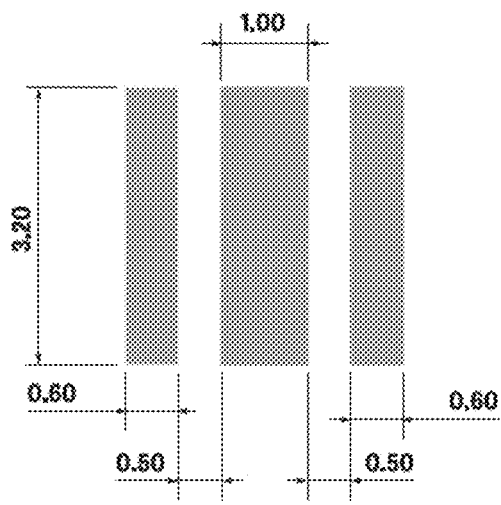
FIG. 6F is an illustration of the solder pattern for the back panels shown in FIGS. 6C and 6D.
Figure 7:
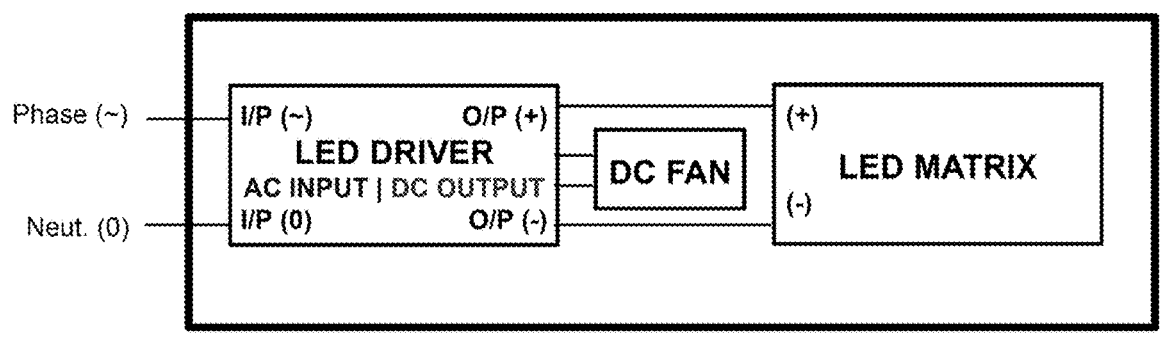
FIG. 7 is a block diagram of the device's circuitry in one embodiment of the present invention, illustrating electrically conductive connections among the circuit (e.g., the LED Driver), the cooling unit in the means for thermal protection (e.g., a fan), and the light array (e.g., the LED matrix).
Figure 8:
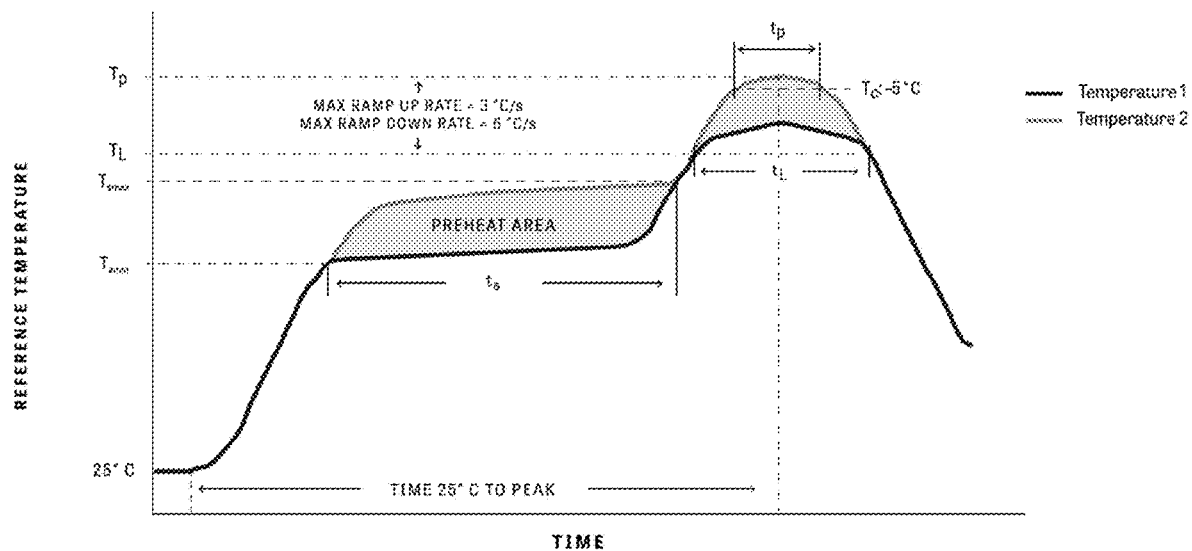
FIG. 8 is a temperature profile of a light source (e.g., an LED) in one embodiment of the present invention.
Figure 9:
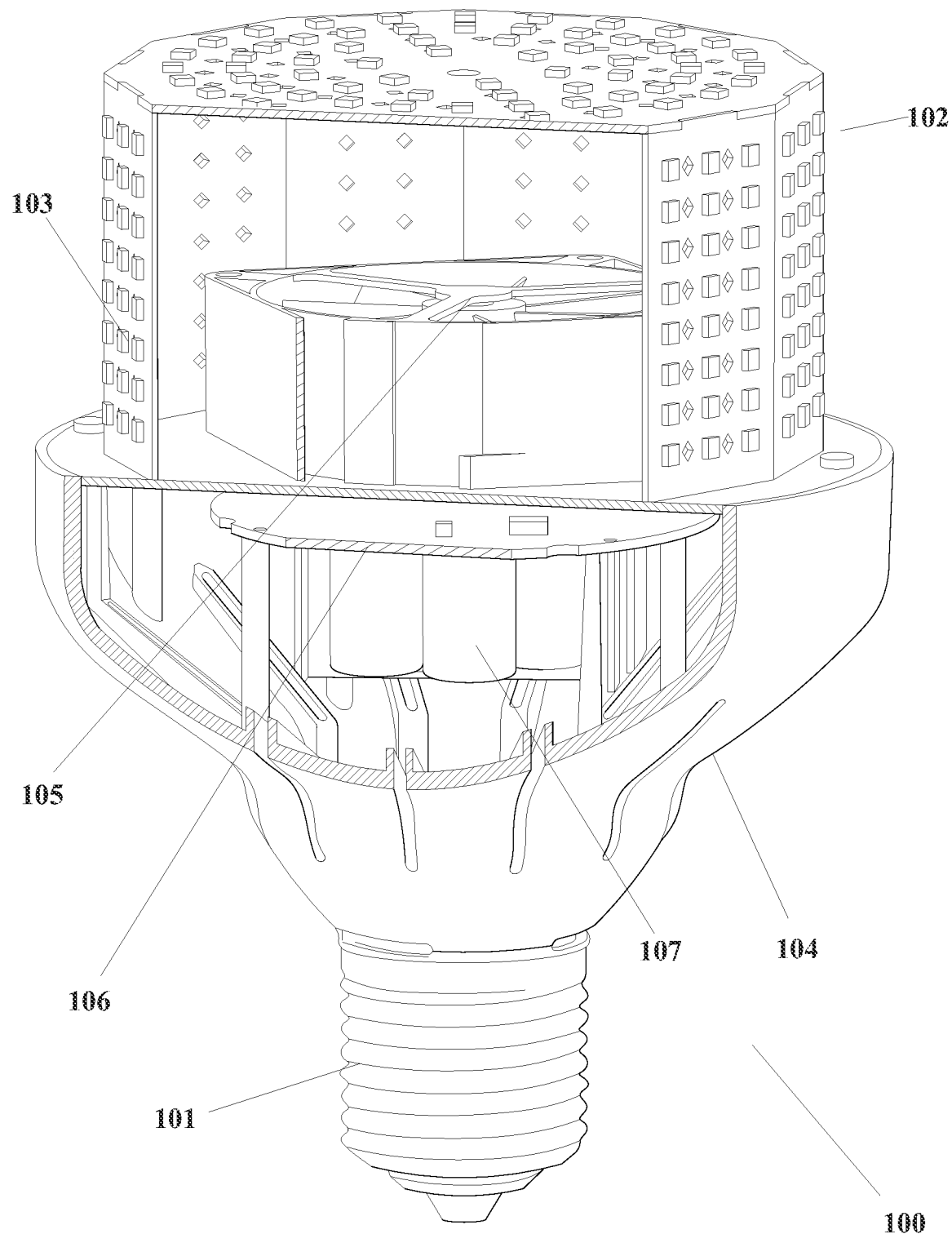
FIG. 9 illustrates the device components in one embodiment of the present invention, including light array (e.g., the LED matrix), the cooling unit in the means for thermal protection (e.g., a fan), the circuit (e.g., the LED driver) and the base.

The present invention provides a disinfection device (100) comprising a base (101); a plurality of light sources (103) arranged in a predetermined pattern to form a light array (102); an ultraviolet light source (103); a bowl-shaped housing (104) having two ends, wherein one end is smaller than the other end, wherein the smaller end of the housing (104) is mounted on the base (101), and the ultraviolet unit is mounted on the other end of the housing (104); a means for thermal protection (105); a means for motion detection (106); and a circuit (107) configured to convert commercial power provided through the base (101) into power for the light array (102), the means for thermal protection (105), and the means for motion detection (106). The means for thermal protection (105), the means for motion detection (106), and the circuit (107) are enclosed within the housing (104). The means for thermal protection (105) maintains the device (100) at an operating temperature that will prevent overheating. The means for motion detection (106) detects motions of a human or animal in proximity to the device (100). After switching on, the light sources (103) emit ultraviolet radiation that projects outwards and disinfects surrounding surfaces and air.

The following terms shall be used to describe the present invention. In the absence of a specific definition set forth herein, the terms used to describe the present invention shall be given their common meaning as understood by those of ordinary skill in the art.

The base (101) is used to receive electrical power. It can be a standard light bulb base (101), also known as an Edison base (101), having a foot electrical contact at the bottom end and a base electrical contact on the side surface with optional screw thread, or any base (101) that is adapted to fit into a standard bulb socket. The base can be unmovably mounted, e.g., by gluing or soldering, onto one typically smaller end of two ends of the housing (104). Two contacts of the base (101) are electrically connected to the circuit (107) so as to provide power to the latter.

The light array (102) comprises a plurality of light sources (103), such as light emitting diodes (LEDs) (103), chosen to emit the desired optical wavelengths from visible to ultraviolet spectrum. When using LEDs as light sources (103), the light array (102) is also termed an LED Matrix (102). The light array (102) may have any shape, such as a cube, a cuboid, a cylinder, a sphere, a disk, or other shape. The light sources (e.g., LEDs) (103) are located on the external surface of the light array (102) and may cover a part or all of the surface. The light sources (e.g., LEDs) (103) are arranged in a predetermined pattern, usually with a fixed spacing for uniform illumination. The light sources (e.g., LEDs) (103) may be chosen to emit ultraviolet rays and visible light simultaneously, and they may mimic daylight, incandescent or fluorescent bulb, and/or provide a particular color tone desired for a practical application. When powered on, the light sources (103) emit light that projects outwards, illuminating and disinfecting surrounding area.

In one embodiment, the ultraviolet source included in the light sources (e.g., LEDs) (103) have peak wavelengths in the range of 260 to 270 nm and total optical power output of at least 60 to 80 mW when operating at 500 mA (see Table 1 below).

TABLE 1

PEAK WAVELENGTH AND TOTAL OPTICAL POWER OUTPUT

| No. | Peak Wavelength (nm) | Minimal Total Optical Power output in mW at 500 mA |
|---|---|---|
| 1 | 260 to 270 | 80 |
| 2 | 260 to 270 | 70 |
| 3 | 260 to 270 | 60 |

In another embodiment, each light source (e.g., an LED) (103) may attain a viewing angle of 130 degrees, a forward voltage between 5.0 and 9.0 V when operating at 500 mA, a junction-to-case thermal resistance of 7.0° C./W, and a power dissipation of 4.0 W or no greater than 4.5 W when operating at 500 mA (see Table 2 below).

TABLE 2

CHARACTERISTICS OF THE LED MATRIX

| Characteristic | Unit | Minimum | Typical | Maximum |
|---|---|---|---|---|
| Viewing Angle | degree | | 130 | |
| Forward Voltage at 500 mA | V | 5.0 | | 9.0 |
| Thermal Resistance (junction to case) | ° C./W | | 7.0 | |
| Power Dissipation at 500 mA | W | | 4.0 | 4.5 |

In one embodiment, the light array (102) can tolerate a continuous forward current of 100 to 700 mA or of 500 mA, a reverse voltage of no higher than about 5 V, a case temperature in the range of −10 to 80° C. when operating at 500 mA, a storage temperature of −40 to 100° C., and a junction temperature no higher than 115° C. (see Table 3 below).

TABLE 3

ABSOLUTE MAXIMUM RATINGS OF THE DEVICE

| Characteristic | Unit | Minimum | Typical | Maximum |
|---|---|---|---|---|
| Forward Current (continuous) | mA | 100 | 500 | 700 |
| Reverse Voltage | V | | | −5 |
| Operating Case Temperature Range at 500 mA | ° C. | −10 | | 80 |
| Storage Temperature | ° C. | −40 | | 100 |
| Junction Temperature | ° C. | | | 115 |

In one embodiment, the light array (102) has a preheat or soak temperature between 150 ($T_{smin}$) and 200° C. ($T_{smax}$) and transitions between the limit temperatures within 60 to 120 seconds. The light array (102) has a liquidous temperature ($T_L$) of approximately 217° C., a maximum peak package body temperature ($T_P$) of 260° C., a maximum ramp-up rate of 3° C./s from, and a time maintained above $T_L$ of 60 to 150 seconds ($t_L$). The light array (102) has a maximum ramp-down rate of 6° C./s from $T_P$ to $T_L$ and a maximum time of approximately 8 minutes from 25° C. to $T_P$ (see Table 4 below).

TABLE 4

PROFILE FEATURE AND PARAMETERS

| Parameter | Value |
|---|---|
| Preheat/Soak Minimum Temperature ($T_{smin}$) | 150° C. |
| Preheat/Soak Maximum Temperature ($T_{smax}$) | 200° C. |
| Maximum Time ($t_s$) from $T_{smin}$ to $T_{smax}$ | 60-120 seconds |
| Maximum Ramp-up Rate ($T_L$ to $T_P$) | 3° C./second |
| Liquidous Temperature ($T_L$) | 217° C. |
| Time ($t_L$) maintained above $T_L$ | 60-150 seconds |
| Maximum Peak Package Body Temperature ($T_P$) | 260° C. |
| Time ($t_P$) within 5° C. of the Specified Temperature ($T_C$) | 30 seconds |
| Maximum Ramp-down Rate ($T_P$ to $T_L$) | 6° C./second |
| Maximum Time 25° C. to Peak Temperature | 8 minutes |

In one embodiment, the light array (102) may have a cylindrical shape with a diameter of 3.5 to 4.5 inches and a height of 6⅛ to 9.5 inches. The light array (102) can have a power of 30 to 150 W, a flux of 10 to 90 μW/cm², and an irradiation of 216 to 1,500 mW (see Table 5 below).

TABLE 5

PRODUCT SIZE, POWER, FLUX AND IRRADIATION

| No. | Diameter (inch) | Height (inch) | Power (W) | Flux (μW/cm²) | Irradiation (mW) |
|---|---|---|---|---|---|
| 1 | 3.5 | 6⅛ | 30 | 10 | 216 |
| 2 | 4.5 | 7 | 30 | 15 | 288 |
| 3 | 4.5 | 9.5 | 100 | 60 | 1,000 |
| 4 | 4.5 | 9.5 | 150 | 90 | 1,500 |

In one embodiment, for enhanced safety of using the device, the ultraviolet light source (103) is not only capable of emitting ultraviolet radiation in the UVC spectrum, it can also emit UVA rays with wavelength in the range of 390 to 410 nm. UVA rays in this range is visible to the human eye, and a subject or a user can thus be aware of the operating status of the device (100) so that the subject or user may avoid elongated exposure to the ultraviolet radiation.

In one embodiment, for enhanced safety of using the device and avoiding exposing a subject/user to the ultraviolet radiation, the ultraviolet light source (103) may simultaneously emit ultraviolet radiation in the UVC spectrum with wavelength in the range of 240 to 290 nm, in the UVA spectrum with wavelength in the range of 390 to 410 nm, and in the visible light spectrum with wavelength longer than 410 nm such as the blue light. Both the UVA rays and the blue light are visible to the human eye. A subject or a user may thus be able to avoid exposure to the UVC rays, when it perceives the UVA rays and/or the blue light.

The circuit (107), also known as an LED driver (107) when driving the LED matrix (102), is an integrated circuit (107) enclosed within the housing (104). The circuit (107) receives power as provided through the base (101) and is configured to convert it into power for the light array (102), the means for thermal protection (105), the means for motion detection (106), and any other component of the device (100) that requires electrical power. The circuit (107) receives sensory signal from the means for motion detection (106), the means for thermal protection (105), and any other sensors equipped with the device (100). Based on sensory signals, the circuit (107) computes and sends control signals. In one embodiment, the circuit (107) sends a control signal to switch the light array (102) off, when it receives sensory signal from the means for motion detection (106) indicating motion of a human in the proximity of the device (100). In one embodiment, the circuit (107) sends a control signal to power up the means for thermal protection (105) when it receives sensory signal indicating that the device (100) is overheated.

The means for motion detection (106) can be a motion sensor (106) normally used in a surveillance apparatus such as a miniaturized security camera. The camera receives electrical power from the circuit (107). The sensory input can be image-based, and the motion sensor (106) can include a camera system that supports normal camera functionality such as capturing visual images. The sensory input can also be infrared ray-based, and the motion sensor (106) can include a sensor unit with predetermined field of view.

The motion sensor (106) transmits sensory signals to the circuit (107), indicating whether motion of a human is detected within a range, e.g., 3 to 5 meters, that is tunable during manufacturing process. In one embodiment, the motion sensor (106) outputs one of two states, i.e., either motion of a human is detected (STATE 1) or no longer detected (STATE 0). As a means for preventing false signals due to noises in surrounding environment, the motion sensor (106) has a built-in sensitivity threshold, such that it only determines that a motion is detected (STATE 1) if the detection signal is above the threshold. The motion sensor (106) also has a built-in time delay, e.g., 3 to 5 seconds, for enhanced safety of use, and the sensory signal may not switch from STATE 1 to STATE 0 before such a time delay has elapsed. The time delay is adjustable during manufacturing process and is sufficiently long for a human user to move to a certain distance away from the device (100) to avoid exposure to UV radiations.

The means for thermal protection (105) is enclosed within the housing (104) and can be a fan (105) that is propelled by a small AC or DC electric motor. The fan (105) may have 6 to 8 blades as shown in the Figures.

In one embodiment, the housing (104) is a bowl-shaped shell (104) providing enclosed components protection and two ends for mounting the base (101) and the light array (102). The housing (104) encloses the circuit (107), the means for thermal protection (105), the means for motion detection (106), and any other component other than the base (101) and the light array (102). The housing (104) has two opened ends, with one end smaller than the other end. The base (101) is mounted onto the smaller end, and the light array (102) is mounted onto the other end. In another embodiment, the housing is a cylinder-shaped. In one embodiment, the housing has two ends and a surface accommodating the light array, wherein the two ends are mounted to the base. In one embodiment, the housing and the base, by "collaborating" with each other, not necessarily as separate components, provide a mechanism to mount the light array in a predetermined pattern while maintaining the functions of the other components.

Conventional UV lights and/or lamps rely on UVC radiation at a wavelength of approximately 254 nm and may only achieve Peak Germicidal Disinfection Effectiveness (PGDE) Index of approximately 80%. Compared to those conventional UV lights and/or lamps, the device (100) of the present invention optimally tunes the wavelength of UVC radiation in the range of 250 to 300 nm and achieves a PGDE Index of almost 100%. In one embodiment, the device achieves a PGDE Index in a range of 85% to 100%. In one embodiment, the device effectively reduces COVID-19 Virus in air duct within the device by 99.9%.

Compared to conventional UV lights/lamps, the disinfection device (100) of the present invention f provides safety protection from UV hazard. Exposure to UV radiation is dangerous and associated with damage to eyesight and incidence of skin cancers, and users of UV lights/lamps should be protected from direct exposure of UV radiation. When operating and emitting UVC radiation, the device (100) of the present invention simultaneously emits UVA radiation and blue light. Both the UVA radiation and blue light are visible to human eyes, such that a user is warned of the device (100) being in operation and avoiding exposure.

The device (100) of the present invention is further equipped with a motion sensor (106) that detect a user's motion. With the device (100) in operation, if the motion sensor (106) detects a user's motion in the proximity of the device (100), it automatically shuts the device (100) down. When a user turns on the device (100), the device (100) can only be turned on when the motion sensor (106) no longer senses the user's motion in proximity of the device (100). The sensitivity of the motion sensor (106) is programmable. A time delay is built in the motion sensor (106), so that after the user turns on the device (100), the device (100) comes into operation only after the time delay lapses, which ensures that the user can be sufficiently far away so that the user is not exposed to the UV radiation.

As another means for improved safety, the device (100) of the present invention may comprise a built-in surge protection device, protecting the device (100) from electrical surge during operation. In one embodiment, the surge protection device is integrated into the base of the device.

The device (100) of the present invention is equipped with a thermal protection (105), e.g., a fan (105) operating on direct current, to lower the device's (100) operating temperature.

The device (100) of the present invention disinfects surrounding surfaces and air circulated through the device (100). Disinfection takes place when air naturally circulates through the device (100). In addition, the device (100) may cooperate with, e.g., external fans and ventilation apparatus for active air circulation.

The device (100) of the present invention may disinfect surfaces and air within a distance of 3 to 5 meters and achieve the almost 100% PGDE Index after a continuous use of 10 to 30 minutes.

The device (100) of the present invention can be equipped in an air duct for disinfecting air circulation inside an HVAC system, air filtering or purification system.

In one embodiment, the present invention provides a solution for surface disinfection through UVC irradiation that can only occur with a line of sight between the UVC Source and the Surface.

In one embodiment, the device (100) aims at surface and air disinfection for airborne viruses.

In one embodiment, the light sources (103) have visible light LEDs on the outside for illumination and UVC LEDs hidden inside for air disinfection. Both the visible light LEDs for illumination and the UVC LEDs for air disinfection can be on simultaneously. Alternatively, when the visible light LEDs for illumination are turned off, the UVC LEDs can stay on and keep disinfecting the air.

Figure 16:
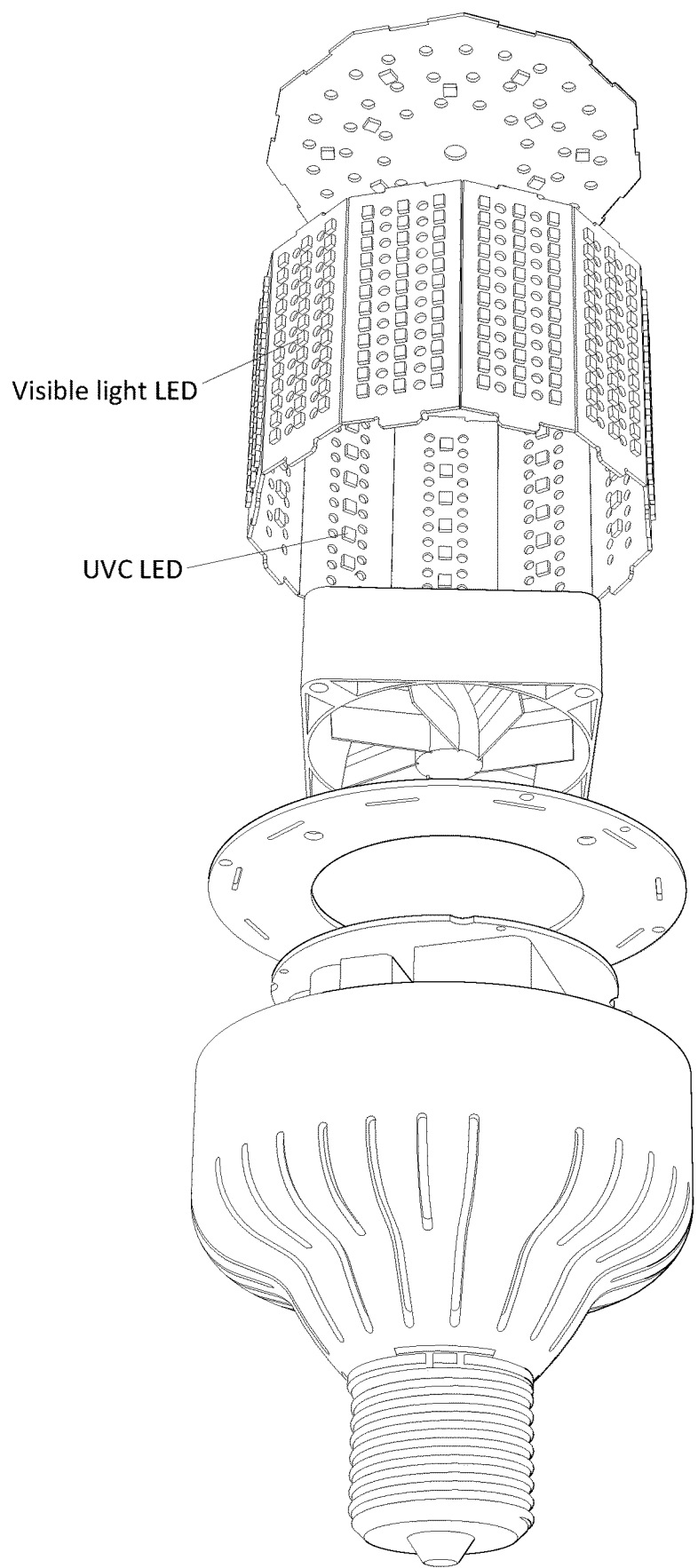
FIG. 16 is an exploded view of a representative device with UVC LEDs inside and visible light LEDs on the outside of the device.

In one embodiment, FIG. 16 shows an exploded view of a representative device (100) with UVC LEDs inside and visible light LEDs on the outside of the device (100).

In one embodiment, the present device (100) has one or more thermal sensors (thermistors) (105) coupled to switches integrated into the LED Driver (107) that senses the critical component's temperature and manages the lamp power to protect it from overheating.

Figure 10:
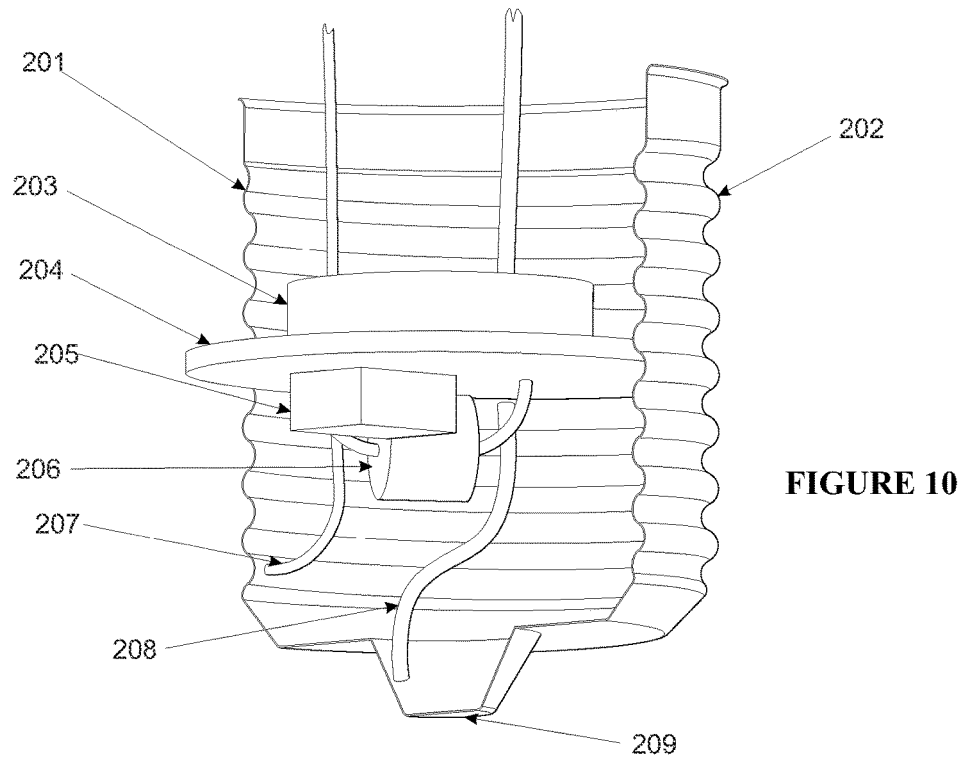
FIG. 10 is a cut-out sketch of the base showing the circuit and electrically conducted connections in the base, wherein 201 is a protective sheet (isolation sheet), 202 is a metal shell (e.g., an Edison Lamp Base Metal Shell), 203 is a metal oxide varistor (MOV) in an SPD, 204 is an SPD Printed Circuit Board (PCB), 205 is a fuse for the SPD, 206 is a Gas Discharge Tube (GDT) or "Arrester" in the SPD, 207 is a common wire (neutral) soldered to 202, 208 is a hot wire (phase) soldered to 209, 209 is a center contact, (e.g., an Edison Lamp Base Center Contact).
Figure 11:
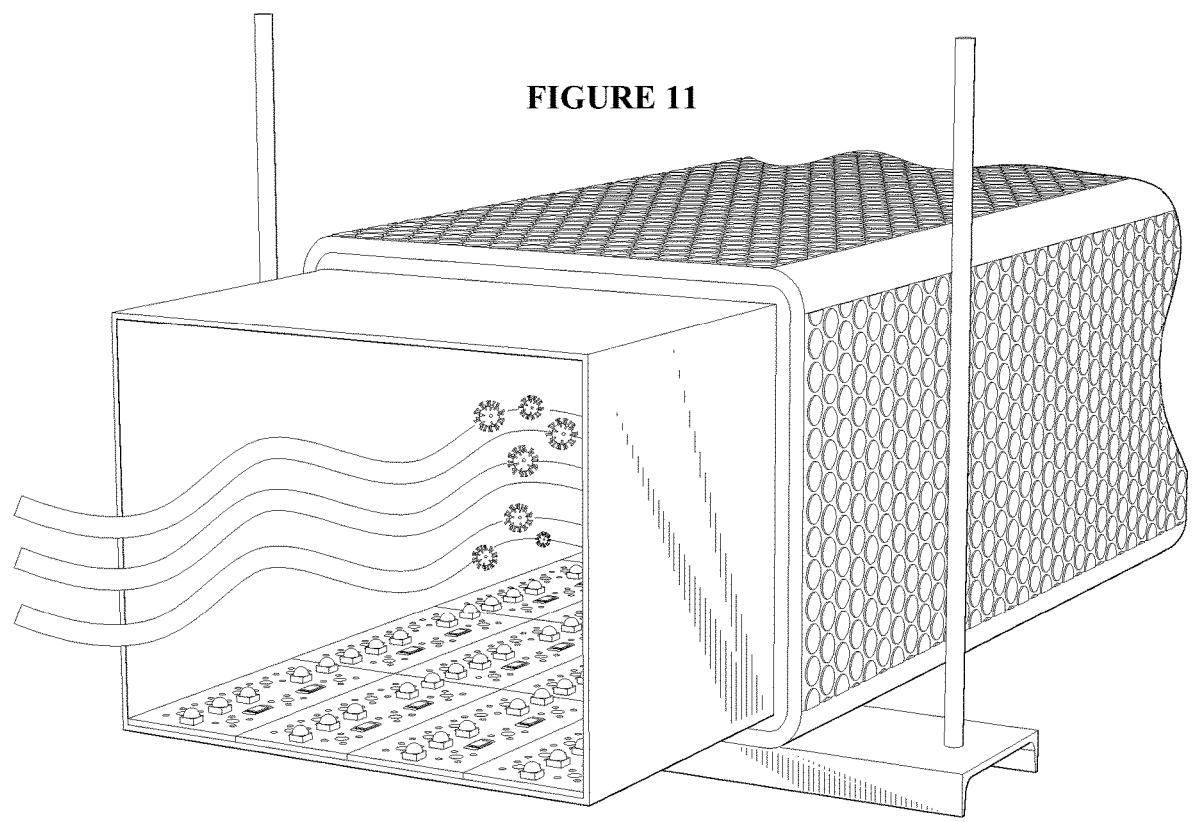
FIG. 11 illustrates an air duct with the device of the present invention equipped therewith for disinfection. Mounted onto the bottom panel of the duct are the light sources that are capable of emitting disinfecting ultraviolet radiation.
Figure 13A:
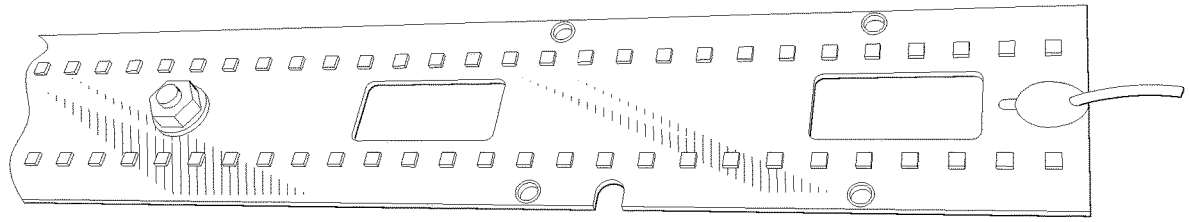
FIG. 13A shows an LED strip comprising the light sources used in the device of the present invention.
Figure 13B:
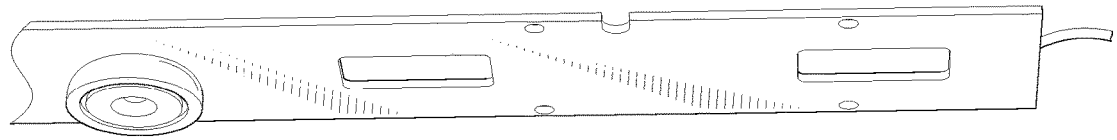
FIG. 13B shows a magnetic strip for mounting the LED strip in FIG. 13A.
Figure 13C:
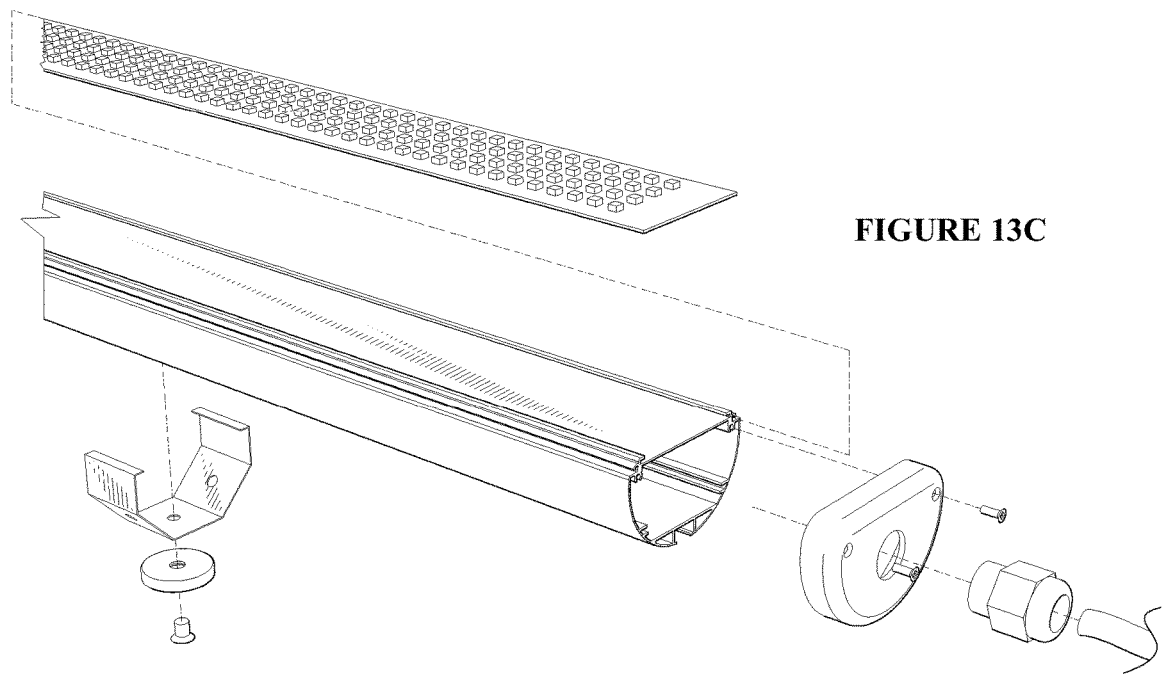
FIG. 13C shows an LED strip comprising a light array arranged in a strip pattern, a housing, a pair of bases, and a unit for mechanically mounting the housing.
Figure 14:
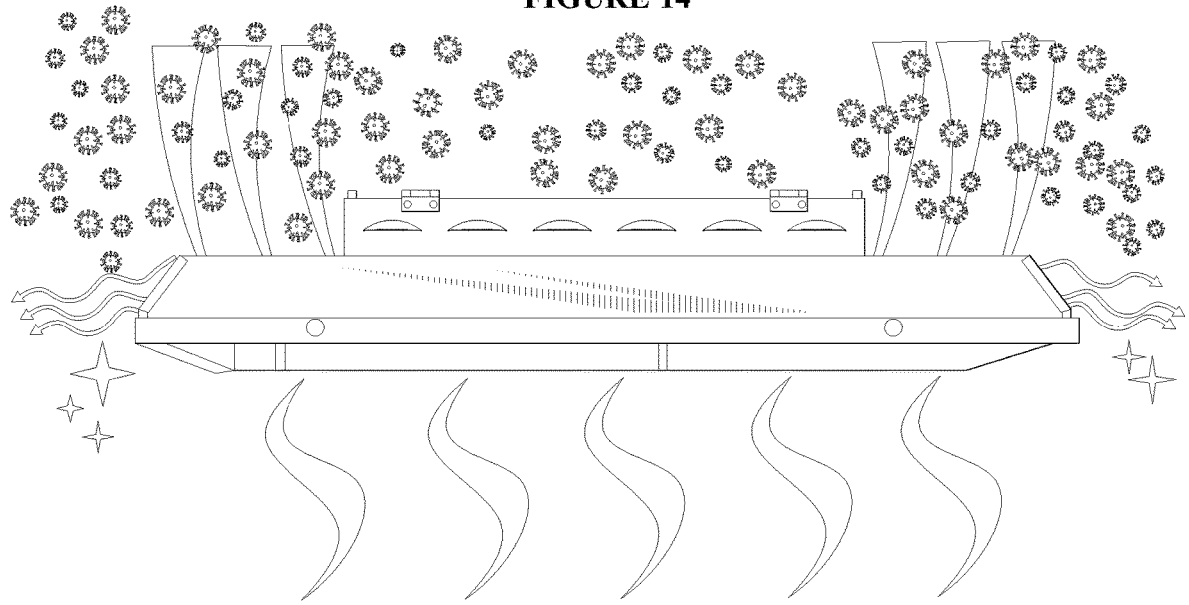
FIG. 14 illustrates an air circulation design that combines the device of the present invention with active air convection for breaking down and killing infectious organisms such as bacteria, viruses, and other pathogens.
Figure 15:
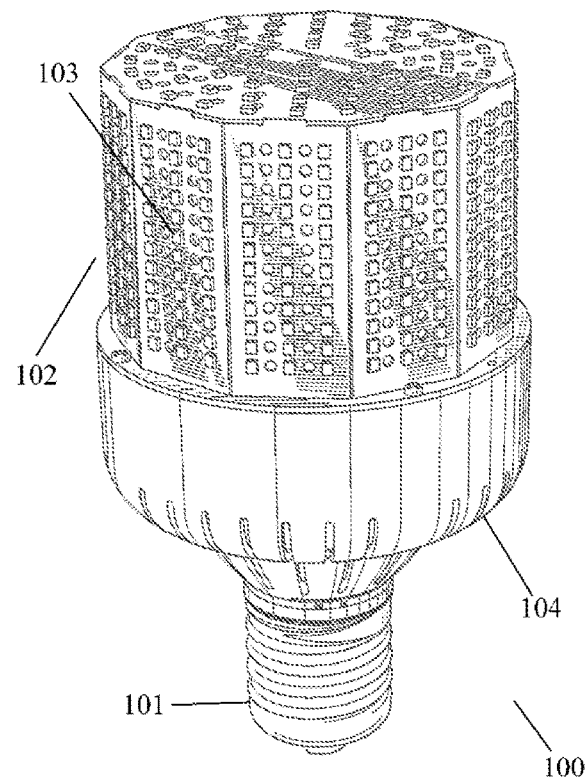
FIG. 15 is a perspective view of one embodiment of the disinfection device of the present invention.

In one embodiment, the present invention illustrates a Surge Protection Device (SPD) built into the base (101) to protect the device (100) from electrical surge. In one embodiment, the SPD comprises an SPD PCB (204) connected to a fuse (205), a metal oxide varistor (MOV) (203), and a GDT or arrester (206) according to a typical configuration in FIG. 10.

In one embodiment, the device (100) of the present invention can be instantly turned on or off. In one embodiment, the wavelength of the UV radiation can be tuned from 250 nm to 285 nm.

In one embodiment, the device (100) has a longer lifetime, approximately 30,000 hours, superior to Quartz UV Tubes and Lamps, which is usually around 8,000 hours.

In one embodiment, the device (100) monitors the airflow inside the air ducts and activates strong enough UVC light (103) to deactivate microorganisms such as bacteria, viruses, and mold.

In one embodiment, the device (100) has a built-in detection of airflow and automatic activation of the UVC light (103). In one embodiment, the device (100) may optionally send fan current in the air handling unit and activate the UVC light (103).

In one embodiment, the instant activation of UVC light (103) only when airflow is being detected may increase the device life by 2 to 3 times or more.

In one embodiment, the device (100) has a built-in wide voltage range 100-480V LED driver (107) for quick and simple installation.

In one embodiment, the device (100) has magnets or clamps mounts.

In one embodiment, the present invention provides a disinfection device comprising:
 a base;
 a plurality of light sources arranged in a predetermined pattern to form a light array;
 a housing having two ends, wherein one end is mounted on the base, and the light array is mounted on the other end;
 a means for thermal protection; and
 a controlling circuit enclosed in the housing and configured to convert electrical power provided through the base into power for the light array, and the means for thermal protection, In one embodiment, the means for thermal protection comprises a thermal sensor for detecting temperature of the device, wherein the thermal sensor is coupled to the controlling circuit, once the temperature reaches or is higher than a predetermined temperature, the controlling circuit provides a signal to prevent the device from overheating; and, after switching on, the light array emits ultraviolet radiation that projects outwards and disinfects surrounding surfaces and air.

In one embodiment, the light sources are light emitting diodes (LEDs).

In one embodiment, the device further comprises a means for motion detection enclosed in the housing, wherein said means for motion detection comprises a motion sensor detecting motion of a person or animal in proximity to the device; when motion of a human or animal is detected, the motion sensor sends a signal to the circuit to switch off the light array.

In one embodiment, the signal provided by the controlling circuit is to adjust the power for the light array, turn on or adjust a cooling unit coupled to the controlling circuit, or both, so as to prevent the device from overheating.

In one embodiment, the cooling unit is a fan enclosed in the housing or base, or inside the light array.

In one embodiment, the circuit is an integrated circuit and works on universal voltage from 100 to 480 volts on an AC power or 120V to 750 volts on a DC power.

In one embodiment, the base, the light array and the housing are mounted with their rotational axes aligned.

In one embodiment, the light array is arranged as an LED strip.

In one embodiment, the ultraviolet radiation has a wavelength in the range of 240 to 290 nm, and a peak wavelength in the range of 260 nm to 270 nm.

In one embodiment, the device further comprises a Surge Protection Device (SPD), which is integrated into the base, protecting the device from electrical surge during operation.

In one embodiment, the ultraviolet radiation has a peak wavelength in the range of 260 nm to 270 nm and each of the light sources in the light array has a total optical power output of at least 60 to 80 mW when operating at 500 mA, or at least 10 to 30 mW when operating at 100 mA.

In one embodiment, the light array has a cylindrical shape with a diameter of 3 to 5 inches and a height of 5 to 10 inches, and the light array has an electric power of 30 to 150 W, a luminous flux of 10 to 90 µW/cm2 at a distance of 1 meter, and a power of irradiation is 200 to 4,500 mW.

In one embodiment, the device has a Peak Germicidal Disinfection Effectiveness (PGDE) Index in a range of 85.0%-100%.

In one embodiment, the device effectively reduces COVID-19 Virus by 99.9% in air within a space irradiated by the device.

In one embodiment, each light source in the light array attains a viewing angle of 90 to 130 degrees, a forward voltage between 5.0 and 9.0 V when operating at 100 to 500 mA, a junction-to-case thermal resistance of 7.0° C./W, and a power dissipation ranging from 4.0 W to 4.5 W when operating at 500 mA or about 1 W at 100 to 150 mA.

In one embodiment, the light array tolerates a continuous forward current of 100 to 700 mA, a reverse voltage of no higher than 5 V, a case temperature in the range of −10 to 100° C. when operating at 500 mA, a storage temperature of −40 to 100° C., and a junction temperature no higher than 115° C.

In one embodiment, the light array simultaneously emits a UVC radiation with a wavelength in the range of 200 to 280 nm and a visible light to human eyes.

In one embodiment, the visible light is UVA rays with a wavelength in the range of 390 to 430 nm, a blue light with a wavelength higher than 410 nm, or both.

In one embodiment, the UVC radiation is emitted from light sources inside of the device for air disinfection while the visible light is emitted from light sources on outside of the device for illumination.

In one embodiment, the motion sensor prevents the device from being switched on until motion of a human or animal is no longer detected after a preset time delay.

In one embodiment, the sensitivity of the motion sensor and the time delay are independently adjustable.

In one embodiment, the present invention provides a disinfection device comprising:
 a pair of bases;
 a plurality of light sources arranged in a strip pattern to form a light array;
 a housing with two ends and a surface accommodating the light array, wherein the housing is mounted to the pair of bases via the two ends;
 a means for thermal protection; and
 a controlling circuit enclosed in the housing and configured to convert electrical power provided through the bases or one of the bases into power for the light array, and the means for thermal protection.

In one embodiment, the means for thermal protection comprises a thermal sensor for detecting temperature of the device, wherein the thermal sensor is coupled to the controlling circuit, once the temperature reaches or is higher than a predetermined temperature, the controlling circuit generates a signal to switch off or adjust the device to prevent the device from overheating; and, after switching on, the light array emits ultraviolet radiation that projects outwards and disinfects surrounding surfaces and air.

In one embodiment, the device further comprises a means for airflow detection detecting airflow passing through or at the device, when the airflow as detected is above a preset and tunable threshold, the controlling circuit generates a signal to power on or adjust the plurality of light sources in the light array.

In one embodiment, the light array arranged in a strip pattern is used in an HVAC system to disinfect air. In one embodiment, the pair of bases comprise a base functioning as a fixing mechanism to mount the light array while the other base, in addition to the fixing mechanism, provides the electrical power for the light array, means for thermal protection, and means for airflow detection. In one embodiment, each base, independently or collaboratively with the other, provides the electrical power for the light array, means for thermal protection, and means for airflow detection.

Throughout this application, various references or publications are cited. Disclosures of these references or publications in their entireties are hereby incorporated by reference into the application in order to more fully describe the state of the art to which this invention pertains. It is to be noted that the transitional term "comprising", which is synonymous with "including", "containing" or "characterized by", is inclusive or open-ended, and does not exclude additional, un-recited elements or method steps.

What is claimed is:

1. A disinfection device comprising:
    a standard lightbulb base;
    a plurality of light sources arranged in a predetermined pattern to form a light array;
    a bowl shaped housing having two ends, wherein one end is mounted on the base, and the light array is mounted on the other end;
    a means for thermal protection enclosed within the housing; and
    a controlling circuit enclosed in the housing and configured to convert electrical power provided through the base into power for the light array, and the means for thermal protection,
wherein the means for thermal protection comprises a thermal sensor for detecting temperature of the device, wherein the thermal sensor is coupled to the controlling circuit, once the temperature reaches or is higher than a predetermined temperature, the controlling circuit provides a signal to prevent the device from overheating; and, after switching on, the light array emits ultraviolet radiation that projects outwards and disinfects surrounding surfaces and air.

2. The device of claim 1, wherein the light sources are light emitting diodes (LEDs).

3. The device of claim 1, further comprising a means for motion detection enclosed in the housing, wherein said means for motion detection comprises a motion sensor detecting motion of a person or animal in proximity to the device; when motion of a human or animal is detected, the motion sensor sends a signal to the circuit to switch off the light array.

4. The device of claim 1, wherein the signal provided by the controlling circuit is to adjust the power for the light array, turn on or adjust a cooling unit coupled to the controlling circuit, or both, so as to prevent the device from overheating.

5. The device of claim 4, wherein the cooling unit is a fan enclosed in the housing or base, or inside the light array.

6. The device of claim 1, wherein the circuit is an integrated circuit and works on universal voltage from 100 to 480 volts on an AC power or 120V to 750 volts on a DC power.

7. The device of claim 1, wherein the base, the light array and the housing are mounted with their rotational axes aligned.

8. The device of claim 1, wherein the light array is arranged as an LED strip.

9. The device of claim 1, wherein the ultraviolet radiation has a wavelength in the range of 240 to 290 nm, and a peak wavelength in the range of 260 nm to 270 nm.

10. The device of claim 1, further comprising a Surge Protection Device (SPD), which is integrated into the base, protecting the device from electrical surge during operation.

11. The device of claim 1, wherein the ultraviolet radiation has a peak wavelength in the range of 260 nm to 270 nm and each of the light sources in the light array has a total optical power output of at least 60 to 80 mW when operating at 500 mA, or at least 10 to 30 mW when operating at 100 mA.

12. The device of claim 1, wherein the light array has a cylindrical shape with a diameter of 3 to 5 inches and a height of 5 to 10 inches, and the light array has an electric power of 30 to 150 W, a luminous flux of 10 to 90 $\mu W/cm^2$ at a distance of 1 meter, and a power of irradiation is 200 to 4,500 mW.

13. The device of claim 1, wherein the device has a Peak Germicidal Disinfection Effectiveness (PGDE) Index in a range of 85.0%-100%.

14. The device of claim 1, wherein the device effectively reduces COVID-19 Virus by 99.9% in air within a space irradiated by the device.

15. The device of claim 1, wherein each light source in the light array attains a viewing angle of 90 to 130 degrees, a forward voltage between 5.0 and 9.0 V when operating at 100 to 500 mA, a junction-to-case thermal resistance of 7.0° C./W, and a power dissipation ranging from 4.0 W to 4.5 W when operating at 500 mA or about 1 W at 100 to 150 mA.

16. The device of claim 1, wherein the light array tolerates a continuous forward current of 100 to 700 mA, a reverse voltage of no higher than 5 V, a case temperature in the range of −10 to 100° C. when operating at 500 mA, a storage temperature of −40 to 100° C., and a junction temperature no higher than 115° C.

17. The device of claim 1, wherein the light array simultaneously emits a UVC radiation with a wavelength in the range of 200 to 280 nm and a visible light to human eyes.

18. The device of claim 17, wherein the visible light is UVA rays with a wavelength in the range of 390 to 430 nm, a blue light with a wavelength higher than 410 nm, or both.

19. The device of claim 17, wherein the UVC radiation is emitted from light sources inside of the device for air disinfection while the visible light is emitted from light sources on outside of the device for illumination.

20. The device of claim 3, wherein the motion sensor prevents the device from being switched on until motion of a human or animal is no longer detected after a preset time delay, and the sensitivity of the motion sensor and the time delay are independently adjustable.

* * * * *